United States Patent [19]

Bathe

[11] Patent Number: 5,752,504
[45] Date of Patent: May 19, 1998

[54] SYSTEM FOR MONITORING THERAPY DURING CALIBRATION

[75] Inventor: Duncan P. L. Bathe, Madison, Wis.

[73] Assignee: Ohmeda Inc., Liberty Corner, N.J.

[21] Appl. No.: 764,569

[22] Filed: Dec. 13, 1996

Related U.S. Application Data

[60] Provisional application No. 60/027,142 Oct. 2, 1996.
[51] Int. Cl.$^6$ ................................................ A61M 15/00
[52] U.S. Cl. ........................... 128/203.12; 128/203.24; 128/203.25
[58] Field of Search ............... 128/203.12, 203.14, 128/203.25, 204.21, 205.23, 202.22, 719, 203.24

[56] References Cited

U.S. PATENT DOCUMENTS

| | | | |
|---|---|---|---|
| 5,253,640 | 10/1993 | Falb et al. | 128/203.12 |
| 5,471,977 | 12/1995 | Olsson et al. | 128/204.21 |
| 5,522,381 | 6/1996 | Olsson et al. | 128/203.12 |
| 5,531,218 | 7/1996 | Krebs | 128/202.22 |
| 5,540,233 | 7/1996 | Larsson et al. | 128/719 |
| 5,558,083 | 9/1996 | Bathe et al. | 128/203.12 |
| 5,615,669 | 4/1997 | Olsson et al. | 128/203.12 |

*Primary Examiner*—Vincent Millin
*Assistant Examiner*—V. Srivastava
*Attorney, Agent, or Firm*—Roger M. Rathbun; Salvatore P. Pace

[57] ABSTRACT

A system for continuing the monitoring of certain gases delivered to a patient during the administration of nitric oxide to provide therapy to the patient. The nitric oxide is controlled by a electrically operated valve that is operated by means of an electrical signal from a CPU. At times when the various gas monitors are being calibrated, the normal alarms based upon those gas monitors are conventionally disabled during that calibration time. With the present invention, the electrical signal to the electrically operated valve is detected at the time the system goes into a calibration cycle and that detected electrical signal is used to establish limits such as a upper limit and a lower limit. Therefore, when the electrical signal to the valve is thereafter monitored and its value exceeds either of those limits, the overall nitric oxide delivery system will activate an alarm to alert the user of an abnormal condition. Thus an alarm system is present even when the various gas monitors are otherwise taken out of the system during their calibration.

12 Claims, 2 Drawing Sheets

SYSTEM FOR MONITORING THERAPY DURING CALIBRATION

The present application is based upon U.S. Provisional patent application Ser. No. 60/027,142, filed Oct. 2, 1996, now abandoned.

BACKGROUND

This invention relates to a system for the administration of inhaled nitric oxide to a patient for therapeutic effects, and, more particularly, to a system that provides a means of monitoring any failure in the therapy system during the calibration of the various monitors that continually monitor the gases involved in such system.

Nitric oxide is used as a method of therapy and is administered to a patient for various therapeutic reasons, among them the treating and preventing of bronchoconstriction or reversible pulmonary vasoconstriction. The therapy is carried out over an extended period of time and may last for periods up to or even exceeding 28-30 days. During such periods it is necessary to recalibrate the various monitors that are continuously monitoring the streams of therapy gases in the system.

In particular, a zero calibration is needed at least once a day and a span calibration should be done about once a month. The zero calibration requires drawing in room air to carry out the calibration and normally may take about five minutes to carry out full calibration. As to the span calibration, the system draws in calibration gases from other sources and may take five or more minutes to calibrate each monitor. Since the span calibration must be made for the NO, $O_2$ and $NO_2$ monitors, that calibration may take up to about 15-20 minutes.

During the time periods in which calibration is taking place, the overall NO administration system is devoid of the normal alarms since the normal monitors are off stream and are not active to carry out the monitoring of the various gases. Due to the sensitivity of the NO administration, it is, of course, extremely important to maintain some alarms or monitoring of the system, particularly in that a toxic substance, $NO_2$, is continuously being generated in the reaction between NO and $O_2$ and its concentration must be maintained below the point where it could cause harm to the patient.

A typical system for NO therapy is shown and described in U.S. Pat. No. 5,558,083 of Ohmeda Inc. and it will be noted that the monitors in that system provide monitoring of the various gases such as NO, $NO_2$, $O_2$ and possibly others. With that system, the delivery of NO is independent of the monitoring of NO and allows for the delivery of NO without monitoring. The principle behind the delivery of NO of that system is the measurement of the patient flow rate and the closed loop control of NO flow rate using a therapy CPU, an NO flow signal, a user inputted NO concentration value and a flow control valve. If a failure occurred, such as a patient flow sensor, under normal operation, the NO monitor would detect the failure by a change in the gas concentration measurement and inform the user by an audible and visual alarm. However, if the NO monitor is being calibrated at that time of the failure and thus not on stream, the above failure would not be detected.

Accordingly, where there are substantial periods of time during calibration when the monitors are basically inoperative, there is a need to provide some alternate system for insuring that the therapy to the patient does not result in increased risk to the patient.

SUMMARY OF THE INVENTION

In accordance with the present invention, a system is provided that continuously allows monitoring of the overall NO administration system even when the monitors are being calibrated and therefore not actively monitoring any of the gases to the patient. The system is initiated when the operator enters the calibration procedure and which sends a signal to the therapy CPU informing it of the lack of gas monitoring. That CPU in normal operation continues to receive a signal in the form of a current that also controls the position of the control valve, i.e. the current to the valve is proportional to the flow through the valve and any change in that current indicates a change in the NO flow and, therefore, a change in the therapy to the patient.

Generally that signal is ignored by the therapy CPU and is not used, however, when the CPU becomes aware of the activation of calibration, it monitors and creates a setting for the current draw at the time the calibration procedure is commenced. The therapy CPU thereafter sets up alarm limits around that initial current value, typical would be a plus or minus 60 percent of the initial current value. The CPU thus continues to monitor that current to the control valve and signals an alarm condition if that current increases or decreases to a value outside the alarm limits set by the CPU and thus alarms on any changes of NO flow in excess of the established limits.

Thus, an alarm is activated and the flow of NO to the patient is continually monitored even during the periods that the gas monitors are basically inactive due to their calibration and the system can continue delivering the therapy to the patient with safety.

DETAILED DESCRIPTION OF THE DRAWINGS

Figure 1:
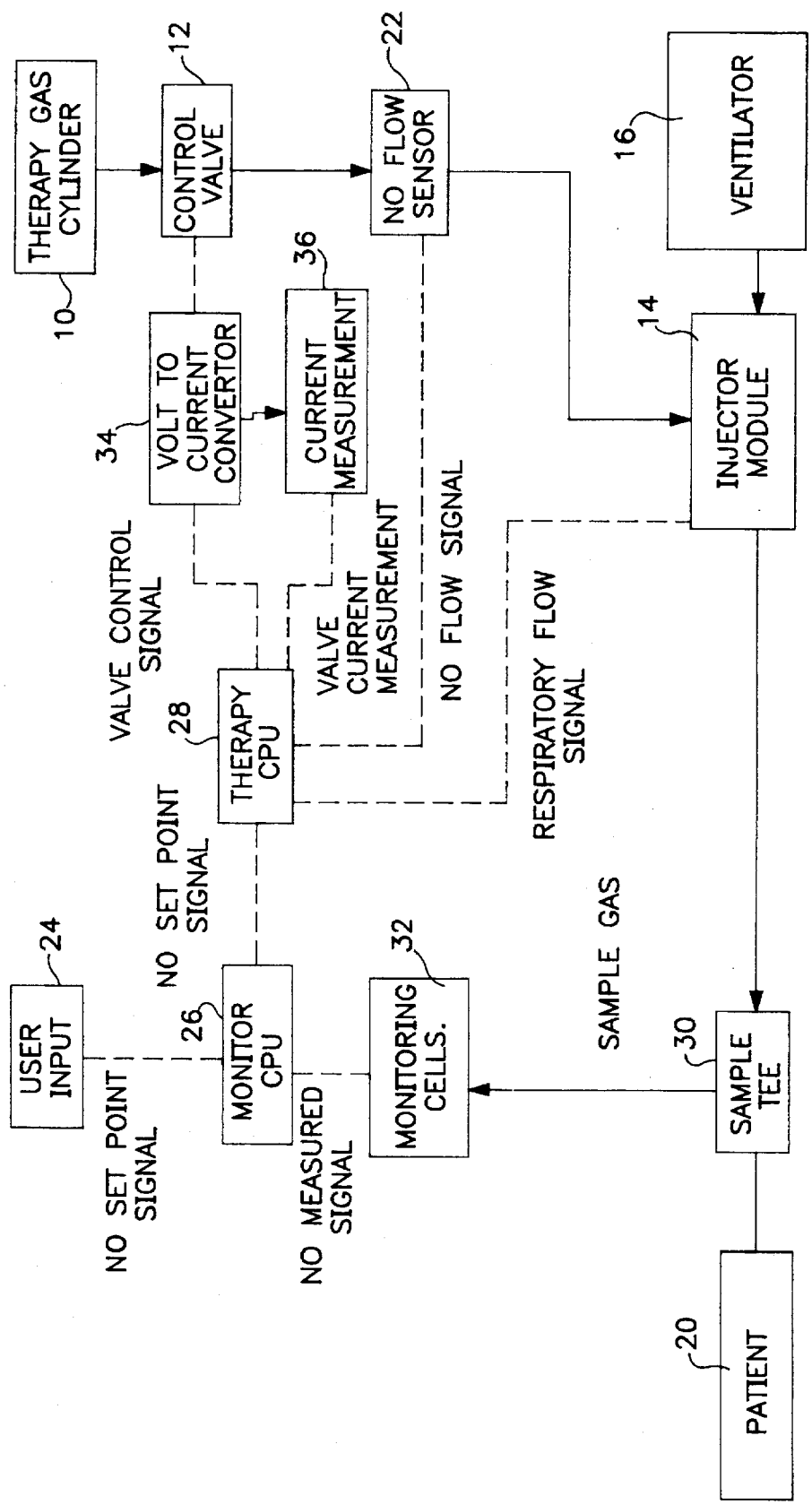
Figure 2:
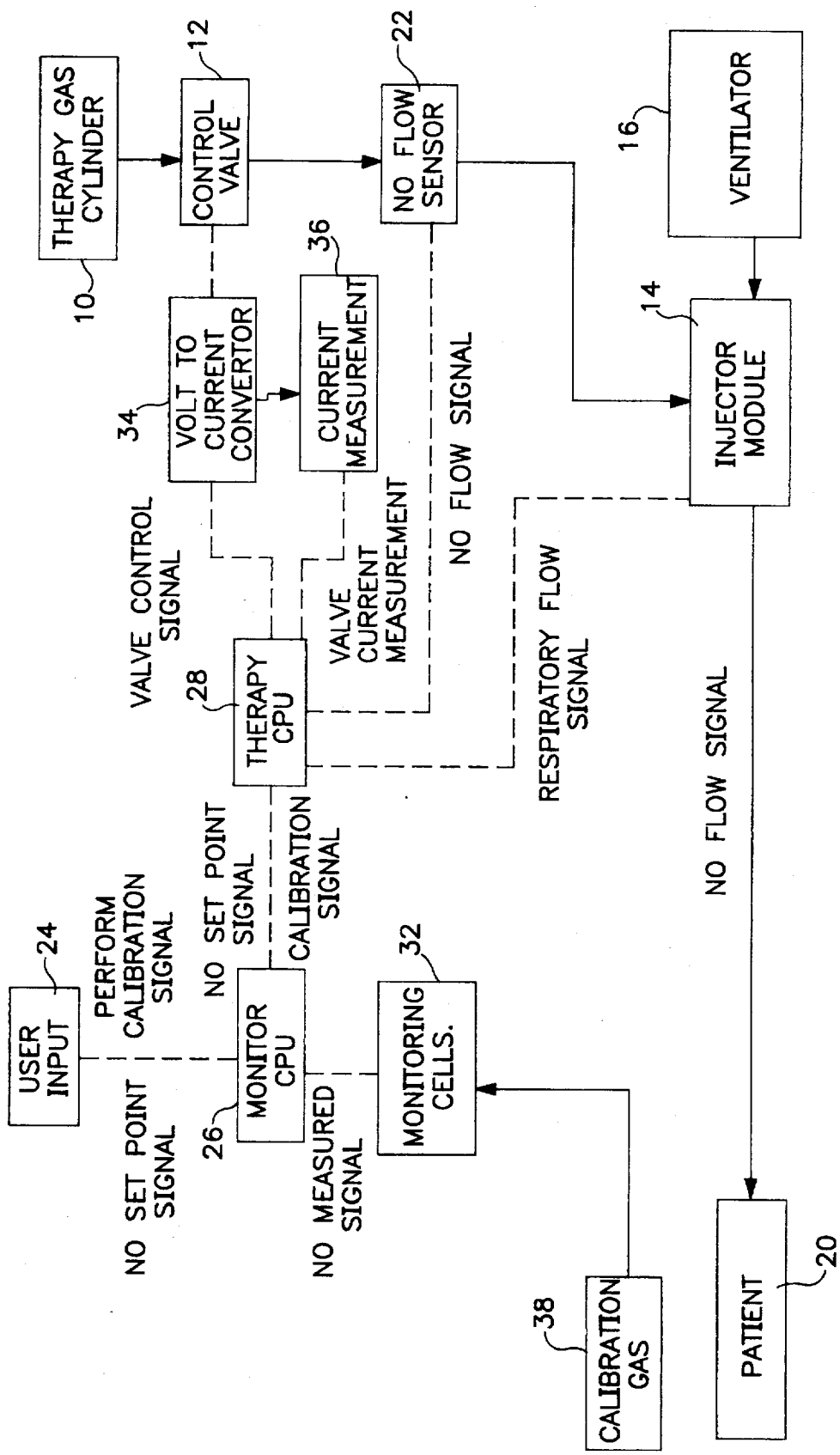

FIG. 1 is a block diagram of a nitric oxide administration system usable with the present invention in its normal operation; and FIG. 2 is a block diagram of the system of FIG. 1 where the system is in its calibration cycle in accordance with the present invention.

DETAILED DESCRIPTION OF THE INVENTION

Turning first to FIG. 1, there is shown a block diagram of the nitric oxide administration system used with the present invention and which is more fully described in U.S. Pat. No. 5,558,083. As shown in FIG. 1, however and which is somewhat simplified with respect to the aforementioned U.S. Patent, a supply of nitric oxide is provided in the form of a cylinder 10 of gas. That gas is preferably nitric oxide mixed with nitrogen and is commercially available in a pressurized cylinder or, may be available from a hospital piping system to supply various locations through out the patient care facility such as operating rooms. The supply of NO may, of course, be mixed with nitrogen or other gases to bring the concentration of NO down to a relatively low level.

A proportion gas control valve 12 is positioned with suitable conduit to receive the NO/nitrogen gas from cylinder 10 and a typical suitable proportional control valve 12 is available from Parker Hannifin Corp., Pneutronics Division, Holis, N.H. and which provides electronic control of gases. The flow of NO/nitrogen is thereafter supplied to an injector module 14 where it is mixed with air or other breathable mixture that is supplied from a gas administration device such as ventilator 16. As again will be seen, although a ventilator is shown, the supply of air or other breathable mixture to the patient may be supplied by a manually squeezed bag or other device to breath the patient The injector module mixes the breathable air from ventilator 16 with the supply of NO/nitrogen from the cylinder 10 in the amount desired by the user for ultimate supply to the patient 20. A flow sensor 22 is normally also present in the NO/nitrogen stream to the injector module 14 to monitor the NO flow.

As more detailed in the aforementioned U.S. Patent, the user selects the desired concentration of NO that is suitable for the patient therapy and inputs that selected concentration by an user input 24 into a monitor CPU 26 as a user set point signal. That signal is then transmitted to a therapy CPU 28 and which controls the proportional control valve 12 by sending a signal to that proportional control valve 12 to set the valve to provide the amount of NO/nitrogen to arrive at the desired concentration of NO administered to the patient.

The value of the electrical valve control signal is determined from an input from a flow sensor in the injector module 14 of the flow to the patient and the desired user input set by the user. With those values, the therapy CPU 28 calculates the correct setting of the proportional control valve 12 and sends the appropriate valve control signal to the proportional control valve 12 to achieve the desired user value.

As a further check of the concentration of NO administered to the patient, a sample tee 30 is provided at a point near the patient and a sample of the gas delivered to the patient is extracted and delivered to various monitoring cells 32 where the monitors, generally electrochemical cells, monitor NO, $O_2$ and $NO_2$. Those monitored values are provided to the monitor CPU 26 to maintained track of the values administered to the patient and to inform the user that the value of NO is within a close range of the value set by the user.

Taking now, the valve control signal that is provided by the therapy CPU 28 to the proportional control valve 12, various electrical or even light signals may be used, however, in the preferred embodiment, a voltage is outputted by the therapy CPU 28 and which is converted to a proportional current in a voltage to current converter 34 and thus a current indicative of the desired position of proportional control valve 12 is inputted to proportional control valve 12. That current is preferably monitored by a current sensing device 36 and that monitored current again inputted to the therapy CPU 28.

Accordingly, as now can be seen, the user determines the desired therapy concentration of NO to be administered to the patient 20 and inputs that value with the user input 24. The user input 24 establishes a signal indicative of the desired NO concentration to the patient and sends that signal to the monitor CPU 26 and on to the therapy CPU 28. In the therapy CPU, a signal is determined that is to be sent to the proportional control valve 12 based on the user input signal and the flow that is being delivered to the patient through injector module 14 so that the proportional control valve 12 can provide the precise amount of NO in nitrogen to arrive at the desired user value to the patient. The signal to the proportional control valve 12 may be an electrical signal in accordance with the preferred embodiment or may be a electromagnetic signal transmitted by a fiberoptic cable or may even be a mechanical transmission.

In the preferred embodiment, the signal from the therapy CPU 28 is in the form of a voltage that is converted to a current in the voltage to current converter 34 and the current transmitted to the proportional control valve 12 to establish the necessary valve setting. As also noted, the current is monitored by the current sensing device 36, however, during normal operation, that value of current is available to the therapy CPU 28 but is not used for any purpose.

Turning now to FIG. 2, there is shown a block diagram of the overall NO administration system when the system is in the calibration mode, that is, the monitoring cells 32 are being calibrated and thus are not available to carry out the continued monitoring of the gases being administered to the patient. In such situation, there is a possibility of a erroneous gas concentration being given to the patient 20 and since one of the gases that is formed with the reaction of $O_2$ and NO is a toxic gas, $NO_2$, the continued monitoring of some kind is needed.

As shown in FIG. 2, therefore, a calibration gas supply 38 is present and which supplies one or more calibration gases to the monitoring cells 32 to ascertain if the monitoring cells are correctly calibrated. For the $O_2$ cell, the calibration gas may be air, however for the other cells, a calibration gas or gases are used containing a concentration of NO, and $NO_2$. In the preferred embodiment the calibration mode is user activated, that is, the user activates the calibration mode by pushing a button or other device on the control panel. Alternatively, of course, the calibration cycle may be timed and a timer continuously tracks the time between calibration and activates the calibration mode at specific intervals.

In either event, when the system goes into calibration mode, a signal is provided to the therapy CPU 28 indicating the initiation of that mode and the therapy CPU 28 immediately determines the magnitude of the signal to it, at that time being transmitted to the proportional control valve controlling the NO/nitrogen gas to the overall system. Thus, the therapy CPU determines and holds that signal value. In the preferred embodiment, that signal is the average current over a ten (10) second period being provided to the proportional control valve 12 to establish the position of that valve. The therapy CPU 28 then establishes a window of values based on the initial value that it has recorded at the time the NO administration system has gone into the calibration mode. As an example, the window may be set at plus or minus 20 percent of the established current average and the therapy CPU 28 sets upper and lower values as alarm limits.

Thus with the alarm limits established, the therapy CPU continues to monitor the current to the proportional control valve 12 throughout the calibration mode and if that current exceed the maximum window value or falls below the minimum window value, an alarm is triggered to alert the user of the condition. That alarm may be audible, visual or both and may also automatically discontinue the administration of NO.

Therefore, as can be seen even though the monitoring cells 32 are being calibrated and thus are no longer actively monitoring the concentration of the gases to the patient 20, the therapy CPU 28 establishes a set point, that of the value to the control signal being sent to the proportional control valve 12, at the time the system is put into calibration mode and the therapy CPU thereafter continues to monitor the signal to the proportional control valve during the calibration mode. If that signal increase above a set cushion above the established value or falls below that cushion, an alarm is triggered to alert the user. Accordingly, even though the normal monitoring cells 32 are inactive, a secondary alarm system is enabled to alert the operator if the proportional control valve 12 is told to change its setting above or below a predetermined amount and thus a monitor is maintained in the NO administration system even when the calibration mode is being activated.

Numerous further variations and combinations of the features discussed above can be utilized without departing from the spirit of the invention as defined by the claims below. Accordingly, the foregoing description of the preferred embodiment should be taken by way of illustration rather than by way of limitation of the invention as claimed.

I claim:

1. A system for providing nitric oxide therapy to a patient, said system having a source of NO containing gas, a source of $O_2$ containing gas, at least one gas concentration monitor and an electrically operated valve for controlling the amount of NO containing gas administered to the patient, a therapy CPU providing an electrical signal for controlling the position of said electrically operated valve and for continuously monitoring the value of the electrical signal provided to said electrically operated valve, the improvement comprising a calibration system to effect the calibration of said at least one gas monitor, means to activate said calibration system whereby said at least one gas concentration monitor is inactivated from monitoring a gas, said means to activate said calibration system providing a signal to said therapy CPU to cause said CPU to detect the value of the electrical signal then being provided to said electrically operated valve by said therapy CPU, means to determine limits of change of said electrical signal with respect to said detected electrical signal value and means to continuously monitor said electrical signal to said electrically operated valve and to provide an alarm signal wherever said monitored electrical signal exceeds said determined limit.

2. A system for providing nitric oxide therapy to a patient as defined in claim 1, wherein said electrical signal is current.

3. A system for providing nitric oxide therapy to a patient as defined in claim 2 wherein said means to monitor said electrical signal monitors the average current over a predetermined period of time.

4. A system for providing nitric oxide therapy to a patient as defined in claim 1 wherein said means to determine said limits is a CPU.

5. A system for providing nitric oxide therapy to a patient as defined in claim 1 wherein said at least one gas monitor monitors NO.

6. A system for providing nitric oxide therapy to a patient as defined in claim 5 said at least one gas monitor monitors NO, $O_2$ and $NO_2$.

7. A system for providing nitric oxide therapy to a patient as defined in claim 1 wherein said limits are set as a high limit above said detected electrical signal and a low limit below said detected electrical signal.

8. A system for providing nitric oxide therapy to a patient as defined in claim 7 wherein said limits are set at about sixty percent above and below said detected electrical signal.

9. A method of providing nitric oxide therapy to a patient, said method comprising the steps of:

providing a source of NO containing gas and a source of $O_2$ containing gas, providing at least one gas monitor for monitoring the concentration of a gas being provided to the patient providing an electrically operated valve for controlling the mixing of NO and O2 to provide a predetermined amount of NO containing gas administered to the patient, providing a therapy CPU having a controllable electrical signal output and communicating the electrical signal to said electrically operated valve, controlling the position of said electrically operated valve by controlling the electrical signal output of the therapy CPU to said electrically operated valve, continuously monitoring the value of the electrical signal output from the therapy CPU to said electrically operated valve calibrating, at selected times, the said at least one gas monitor by inactivating the said at least one gas monitor and passing a calibration gas therethrough, detecting the value of the electrical signal then being provided to the electrically operated valve by said therapy CPU when said at least one gas monitor is selected for calibration, determining limits of change of the electrical signal with respect to the detected value of the electrical signal and continuously monitoring the electrical signal from the therapy CPU to the electrically operated valve, and activating an alarm wherever the value of the electrical signal from the therapy CPU to the electrically operated valve exceeds the limits of change determined in the previous step.

10. A method of providing nitric oxide therapy to a patient as defined in claim 9 wherein said step of determining limits of change determines both a maximum positive change and a negative signal change with respect to the detected signal value.

11. A method of providing nitric oxide therapy to a patient as defined in claim 9 wherein said step of continuously monitoring the electrical signal value monitors current.

12. A method of providing nitric oxide therapy to a patient as defined in claim 11 wherein said step of continuously monitoring the electrical signal value monitors the average current over a predetermined period of time.

* * * * *